(12) United States Patent
Hogan et al.

(10) Patent No.: US 8,577,432 B2
(45) Date of Patent: Nov. 5, 2013

(54) NOISE TOLERANT MEASUREMENT

(76) Inventors: Josh N. Hogan, Los Altos, CA (US);
Gaston D Baudat, Glenmoore, PA (US)

( * ) Notice: Subject to any disclaimer, the term of this patent is extended or adjusted under 35 U.S.C. 154(b) by 1022 days.

(21) Appl. No.: 12/584,666

(22) Filed: Sep. 9, 2009

(65) Prior Publication Data

US 2010/0063370 A1    Mar. 11, 2010

Related U.S. Application Data

(60) Provisional application No. 61/191,569, filed on Sep. 10, 2008.

(51) Int. Cl.
*A61B 5/1455* (2006.01)
(52) U.S. Cl.
USPC ............... 600/310; 600/473; 600/476
(58) Field of Classification Search
USPC ............ 600/310, 316, 322, 473, 476
See application file for complete search history.

(56) References Cited

U.S. PATENT DOCUMENTS

| 6,725,073 | B1 * | 4/2004 | Motamedi et al. | 600/316 |
| 7,289,835 | B2 * | 10/2007 | Mansfield et al. | 600/316 |
| 8,064,975 | B2 * | 11/2011 | Pav | 600/323 |

* cited by examiner

*Primary Examiner* — Eric Winakur

(57) ABSTRACT

The invention relates to statistical methods for fitting a mathematical model of the interaction of signals, such as optical signals, with tissue to detected signals or data related to the interaction. In particular it relates to statistical methods for fitting a mathematical model of the interaction of optical signals with tissue to actual signals, such as interferometric signals related to data optical scattering in tissue and their relationship to glucose concentration. It also relates to statistical methods for fitting a mathematical model of the interaction of optical signals with tissue to data such as the spectral distribution values of optical signals absorbed or scattered by tissue and their relationship to glucose concentration. The invention provides a practical non-invasive glucose measurement method and system. The invention also provides a measurement method and system that performs well in low signal-to-noise environments.

5 Claims, 4 Drawing Sheets

NOISE TOLERANT MEASUREMENT

RELATED APPLICATIONS

This patent application, claims priority from provisional patent application 61/191,569 filed on 10 Sep. 2008. This application relates to U.S. utility Pat. No. 7,526,329 titled "Multiple Reference Non-Invasive Analysis System", and to U.S. utility patent application Ser. No. 11/048,694 filed on 31 Jan. 2005 titled "Frequency Resolved Imaging", which is a continuation in part of U.S. Pat. No. 7,526,329. The contents of both U.S. Pat. No. 7,526,329 and Ser. No. 11/048,694 are incorporated herein by reference as if fully set forth herein. This application also relates to U.S. utility patent application Ser. No. 12/214,600, filed on 21 Jun. 2008, titled "Orthogonal Reference Analysis System with Enhanced SNR" which is incorporated herein by reference as if fully set forth herein.

FIELD OF THE INVENTION

This patent application, relates to bio-medical measurements of tissue including in-vivo measurements. In particular the invention relates to non-invasive measurements of analytes and more particular to measurement of glucose.

BACKGROUND OF THE INVENTION

Glucose concentration in humans and other entities can be measured non-invasively using optical coherence tomography (OCT). OCT typically uses a super-luminescent diode (SLD) as the optical source, as described in Proceedings of SPIE, Vol. 4263, pages 83-90 (2001). The SLD output beam has a broad bandwidth and short coherence length.

The OCT technique involves splitting the output beam into a probe and reference beam. The probe beam is applied to the system to be analyzed (the target). Light scattered back from the target is combined with the reference beam to form the measurement signal. Because of the short coherence length only light that is scattered from a depth within the target such that the total optical path lengths of the probe and reference are equal combine interferometrically. Thus the interferometric signal provides a measurement of the scattering value at a particular depth within the target. By varying the length of the reference path length, a measurement of the scattering values at various depths can be measured and thus the scattering value as a function of depth can be measured.

An alternative approach which generates interference signals from multiple depths simultaneously or concurrently is described in U.S. utility Pat. No. 7,526,329 and patent application Ser. No. 11/048,694 incorporated herein by reference. Scattering profile information can be generated by processing these interference signals.

The correlation between blood glucose concentration and optical scattering by tissue has been reported in Optics Letters, Vol. 19, No. 24, Dec. 15, 1994 pages 2062-2064. The change of the scattering coefficient correlates with the glucose concentration and therefore measuring the change of the scattering value with depth (or scattering profile) provides a measurement of the scattering coefficient which provides a measurement of the glucose concentration.

The glucose concentration is typically determined by plotting the OCT signal on a logarithmic (log) scale and calculating the glucose concentration from the slope of the resulting trace. Typically the slope of the signals is calculated at specific depths by a linear least-squares method, such as, least-square linear fit.

This approach of taking the log of the OCT signal also modifies noise associated with the OCT signal which can introduce significant error in the glucose concentration measurement leading to a lack of accuracy in the glucose measurement. The log approach compresses the noise for small values and inflates it for large ones, resulting in poor line fitting results. The poor fit and consequential lack of accuracy is particularly troublesome in the low signal to noise ratio (SNR) environment typical in non-invasive glucose monitoring.

There is therefore an un-met need for a noise tolerant measurement or calculation system or method that is robust in a low SNR environment. Further there is also an un-met need for such a noise tolerant glucose measurement or calculation system or method that is robust in a low SNR environment. Measurement systems other than OCT, such as spectral analysis systems, also have an un-met need for a noise tolerant measurement or calculation system or method that is robust in a low SNR environment.

SUMMARY OF THE INVENTION

The invention taught herein meets at least all of the aforementioned un-met needs. The invention relates to statistical methods for fitting a mathematical model of the interaction of signals, such as optical signals, with tissue to detected signals or data related to the interaction. In particular it relates to statistical methods for fitting a mathematical model of the interaction of optical signals with tissue to actual signals, such as interferometric signals related to data optical scattering in tissue and their relationship to glucose concentration.

It also relates to statistical methods for fitting a mathematical model of the interaction of optical signals with tissue to data such as the spectral distribution values of optical signals absorbed or scattered by tissue and their relationship to glucose concentration. It also relates to statistical methods for fitting a mathematical model of the interaction of both optical and acoustic signals with tissue to data such as the propagation speed values of acoustic signals in tissue and their relationship to glucose concentration.

In a system according to the preferred embodiment, the invention provides a non-invasive analysis system which is comprised of an actual analysis system, a system model, a noise model, a parametric estimation and an output means. The actual analysis system outputs at least one actual signal which contains information obtained from a target of interest. In the preferred embodiment the target of interest is human tissue and the analyte of interest is glucose.

In the preferred embodiment the actual signals are interferometric signals created by an OCT measurement system. The interferometric signals are detected as analog signals and typically digitized and undergo pre-processing where such pre-processing may include filtering and the like. Output from the actual measurement system, referred to herein as actual signals, is sent to the parametric estimation processor.

In the preferred embodiment a system model, also referred to as a parametric model, generates and outputs at least one theoretical signal which is also sent to the parametric estimation processor. The theoretical signals generated by the system model are an ideal representation of the signals resulting from the interaction of radiation from an ideal analysis system with an ideal target. From the system model, theoretical signals can be calculated and sent to the parametric estimation processor. The actual signals and theoretical signals may differ due to noise and may differ as a result of simplifying assumptions of the model.

The invention also provides for a noise model which outputs noise statistics. These noise statistics can be generated by analyzing actual noise or may be derived from a theoretical model of various noise sources (e.g. optical source noise, mechanical noise, target noise, motion noise, detector noise, electronic noise, etc.) or some combination of the actual noise and theoretical models. The noise statistics output by the noise model are sent to the parametric estimation processor.

The parametric estimation processor, which may be a micro-processor or DSP (digital signal processor), such as an ARM or one of the Blackfin processor family manufactured by Analog Devices, receives the actual signals, the theoretical signals and the noise statistics. The parametric estimation processor adjusts the parameters of the system or parametric model so that the difference between the actual and theoretical signals matches the characteristics of the predicted or measured noise.

Adjusting the parameters of the system model to get a best fit between the actual signals and the theoretical signals and to best match the noise characteristics of the predicted or measured noise yields an optimal value of one or more system model parameters. In the preferred embodiment the invention provides a method and system for robust non-invasive measurement of glucose concentration using estimation techniques to optimize the fit to measured data. The parametric estimation processor also outputs information about at least one attribute of the target of interest. In the preferred embodiment the parametric estimation processor outputs a glucose concentration value which may be stored or displayed.

The inventive approach performs particularly well in a noisy environment, such as is typical of living or biological systems. The invention thus provides a non-invasive, accurate and robust measurement, particularly in a low SNR environment. Accurate glucose measurements are useful in medical treatment to control glucose levels of people with diabetes.

The preferred inventive method provides a means for processing signals detected by a non-invasive analysis system to determine the value of at least one attribute of a target in a noisy or low signal to noise environment. The steps of the method are: generating a parametric model that represents the interaction of radiation scattered by the target and at least one reference signal associated with the non-invasive analysis system; generating a noise model, that is comprised of the noise associated with the non-invasive analysis system (system noise), the noise associated with the target (target noise) and the noise associated with the scattered radiation (radiation noise); generating a formula with a number of parameters, at least one of which is related to the attribute of the target, the value of which attribute is to be determined; and using estimation techniques to fit processed (or pre-processed) signals detected by the non-invasive analysis system to determine the value of the attribute of the target.

The invention can be used in measurement systems other than OCT, such as spectral analysis systems, which also have an un-met need for a noise tolerant measurement or calculation system or method that is robust in a low SNR environment.

DETAILED DESCRIPTION OF THE INVENTION

A preferred embodiment of this invention involves generating a parametric model (also referred to herein as a system model) that represents the interference signals (or functions of the interference signals) generated by the interaction of an optical beam or light (also referred to as radiation) scattered from within the target and reference signal or signals associated with a non-invasive analysis system that is used to determine the attribute of a target. In the preferred embodiment the target is tissue, blood or a tissue fluid such as interstitial fluid. In the preferred embodiment the attribute to be determined is glucose concentration.

Figure 1:
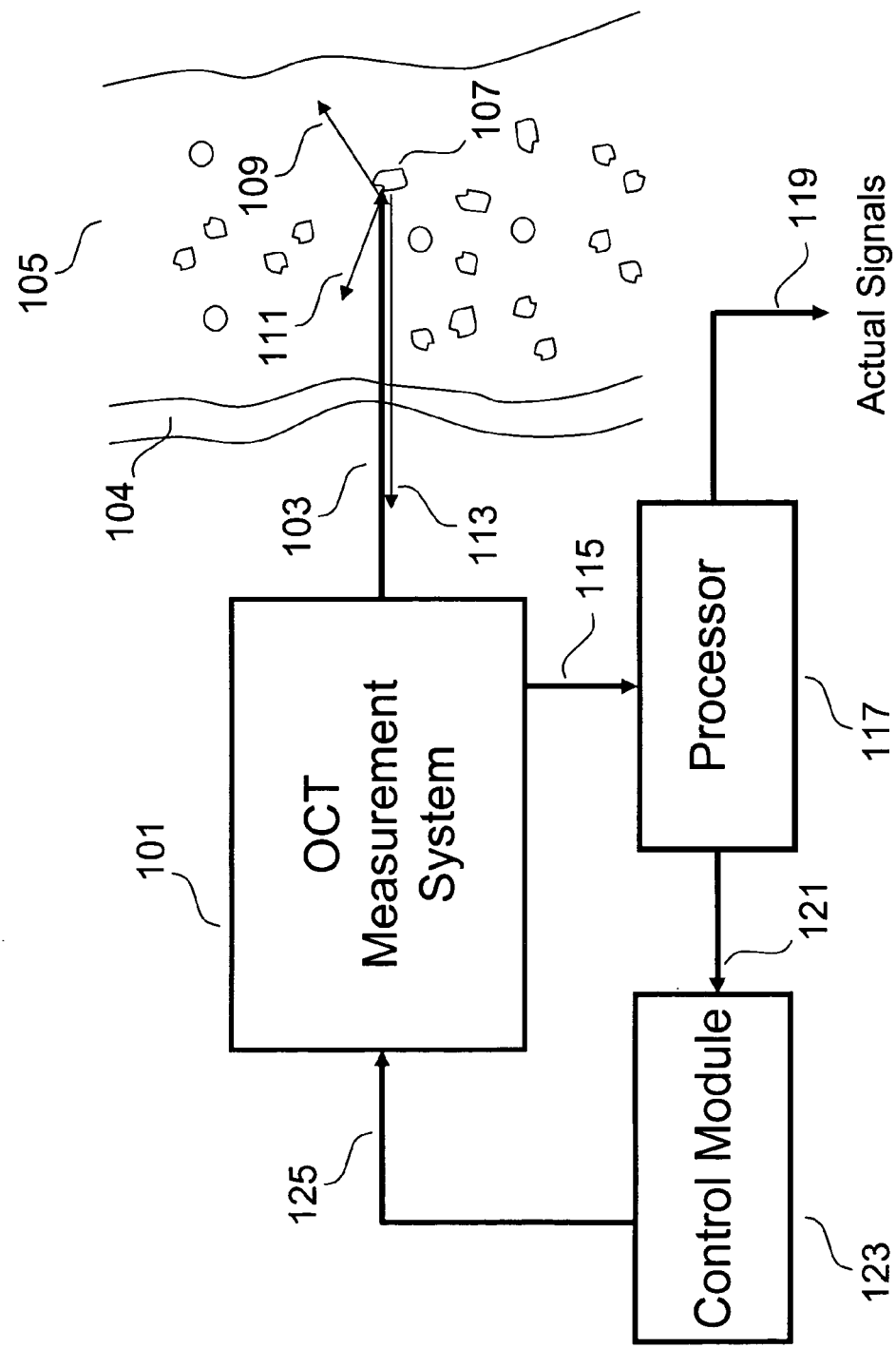
FIG. 1 is an illustration of an actual analysis system, such as OCT system analyzing tissue and generating actual signals that contain glucose-related information.
Figure 2:
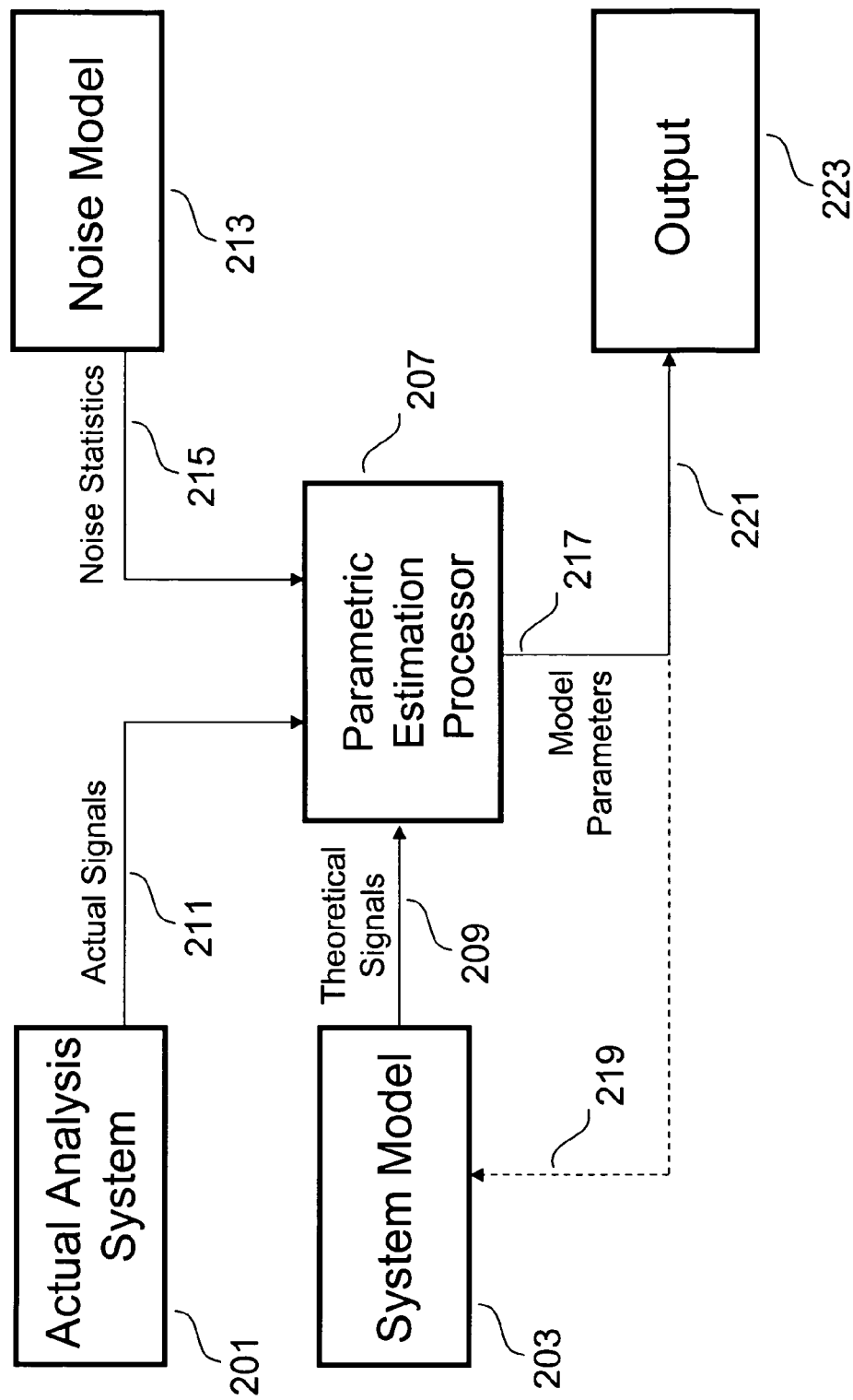
FIG. 2 is an illustration of a non-invasive analysis system which is comprised of an actual analysis system, a system model, a noise model, a parametric estimation processor and an output means according to the invention.

The preferred embodiment is illustrated in and described with respect to FIGS. 1 and 2. In FIG. 1 an OCT measurement system 101 directs light 103 through the skin 104 into the tissue target 105. For purposes of this invention tissue includes all components associated with human tissue including, but not limited to, cells, cell membranes, interstitial fluid and blood.

Light is scattered due to refractive index discontinuities at boundaries of tissue components (e.g. component 107). The scattered light can be in any direction, indicated by 109 and 111. Some light is back-scattered substantially along the direction 113 of the light directed at the tissue, to generate interference signals in the OCT measurement system 101.

The resulting optical interference signals are detected by one or more detectors to produce analog electrical signals 115, which are typically digitized and which typically under go some processing, also referred to as pre-processing, in a processing module 117. The resulting pre-processed digital signals contain glucose related information and are referred to herein as actual signals.

The processor 117 may also provide feedback signals 121 to a control module 123 which controls the performance of the OCT measurement system 101 by means of control signals 125. Such control signals can include, but are not limited to, temperature control signals, one or more piezo drive signals and signals to control lateral scanning of the OCT measurement system 101. The combination of the measurement system 101, the processor 117 and the control module 123 is referred to herein as the actual analysis system 201.

A non-invasive analysis system according to the preferred embodiment is illustrated in and described with respect to FIG. 2. The analysis system is comprised of an actual analysis system 201, a system model 203, a noise model 205, a parametric estimation processor 207 and an output means 223. The actual analysis system outputs at least one actual signal 211 which contains information relating to an analyte of interest obtained from a target of interest. In the preferred embodiment the target of interest is human tissue and the analyte of interest is glucose.

In the preferred embodiment the actual signals are interferometric signals created by an OCT measurement system. The interferometric signals are detected as analog signals and typically digitized and undergo pre-processing where such pre-processing may include filtering and the like. Output from the actual measurement system, referred to herein as actual signals 211, is sent to the parametric estimation processor 207. The actual measurement system is also referred to herein as an actual analysis system 201.

The system model 203 (also referred to as the parametric model) in the preferred embodiment generates and outputs at least one theoretical signal 209 which is also sent to the parametric estimation processor 207. The theoretical signals generated by the system model 203, are an ideal representation of the signals resulting from the interaction of radiation from an ideal analysis system with an ideal target. From the system model 203 theoretical signals can be calculated and sent to the parametric estimation processor 207. The actual signals and theoretical signals may differ due to noise and may differ as a result of simplifying assumptions of the model.

The invention also provides for a noise model 213 which outputs noise statistics 215. These noise statistics can be generated by analyzing actual noise or may be derived from a theoretical model of various noise sources (e.g. optical source noise, mechanical noise, target noise, motion noise, detector noise, electronic noise, etc.) or some combination of the actual noise and theoretical models. The noise statistics 215 output by the noise model 213 are sent to the parametric estimation processor 207.

The parametric estimation processor 207, which may be a micro-processor or DSP (digital signal processor), such as an ARM processor or a processor of the Blackfin family manufactured by Analog Devices, receives the actual signals 211, the theoretical signals 209 and the noise statistics 215. The parametric estimation processor 207 adjusts the parameters of the system or parametric model so that the difference between the actual and theoretical signals matches the characteristics of the predicted or measured noise.

Adjusting the parameters of the system model to get a best fit between the actual signals and the theoretical signals and to best match the noise characteristics of the predicted or measured noise yields an optimal value of one or more system model parameters 217. Adjusting the parameters of the system model to get a best fit between the actual signals and theoretical signals and also to match the statistical characteristics of difference between the actual and theoretical signals noise characteristics of the predicted or measured noise yields an optimal value of one or more system model parameters.

This adjustment of parameters may be an iterative process with repeated optimization of one or more parameters and feeding back one or more adjusted model parameters 219 to the system model 203. The system model may be dynamically selected from a set of pre-existing model templates (e.g. based on skin type, gender or other characteristics of the target). The system model may be generated based on an understanding of the physics of the light interacting with the target. The system model may be empirically generated by analyzing data sets, such that a pattern is found dynamically without necessarily being predicated on the operative physics. It can also be appreciated that various combinations of understanding of the operative physics along with iterative outputs of the parametric processor using signals from multiple targets where multiple targets may include multiple target sites on the same individual and target sites on multiple individuals or any combination thereof.

In the preferred embodiment estimation techniques to optimize the fit to measured data and noise characteristics, include but are not limited to: maximum likelihood techniques; least mean square techniques; weighted least mean square techniques; Bayesian inference; minimum of margin.

At least one of the model parameters 221 which contains information about at least one attribute of the target of interest, is also sent to an output module 223. The model parameter 221, which in the preferred embodiment is a glucose concentration related parameter, may be stored, displayed or made available for other operations which include, but are not limited to: controlling a device such as an insulin pump; or causing a cell phone to send a text message or pre recorded message; or controlling operation of a consumer device, such as an iPOD.

Figure 3:
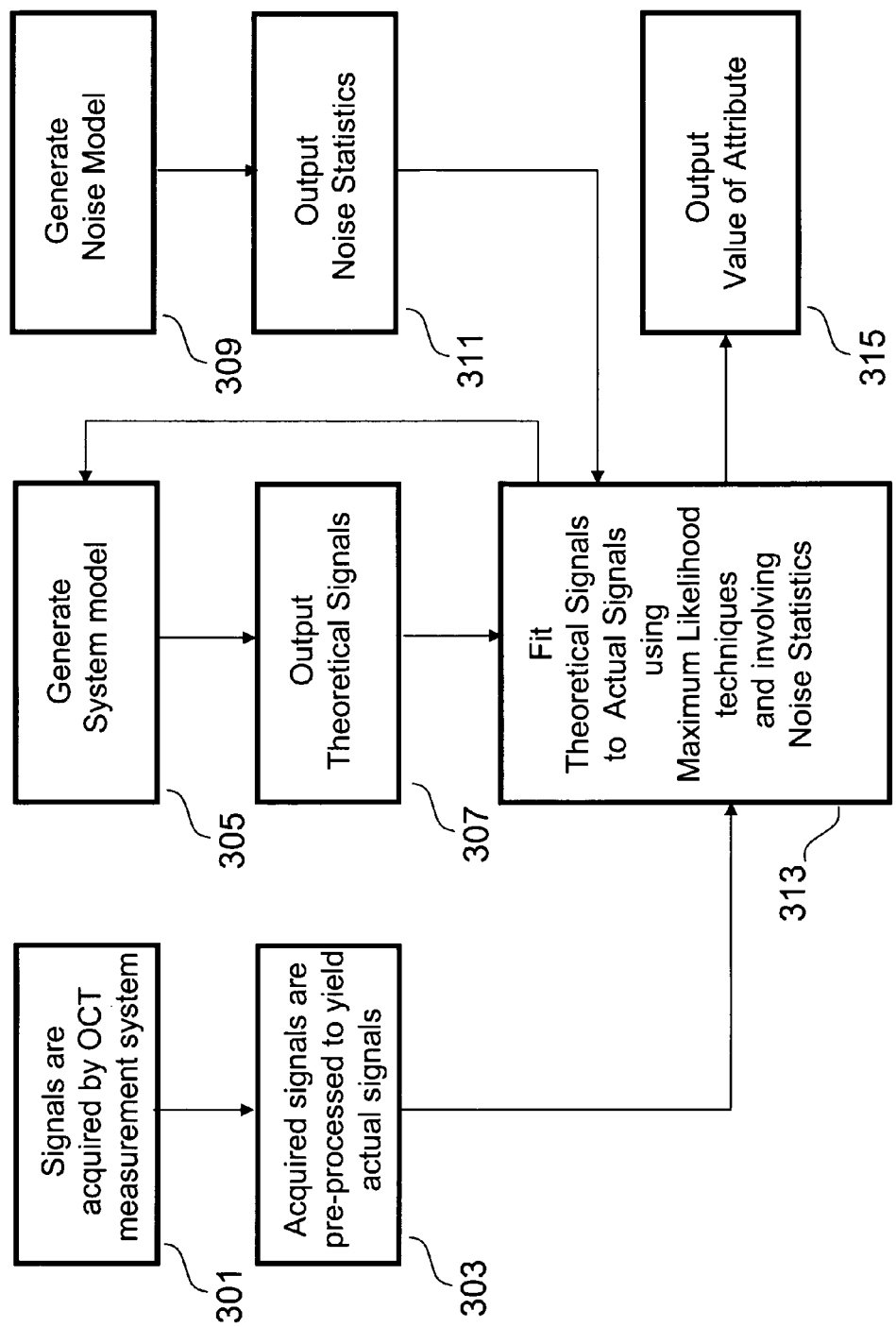
FIG. 3 is a flow chart depicting the steps taken to achieve accurate measurement of an attribute or parameter in a low SNR environment according to the invention.

A preferred embodiment is further described with respect to the flow chart in FIG. 3 which depicts the following steps: One or more interference signals are acquired by the OCT measurement system 301 as a result of being detected by one or more opto-electronic detectors. In the preferred embodiment the interference signals may be composite interference signals containing information related to multiple depths within the target of interest (as described in patents and applications incorporated herein by reference).

Acquired signals are pre-processed to yield actual signals 303. The detected interference signals are pre-processed (also referred to as processed). The resulting pre-processed signals are referred to herein as actual signals. Such pre-processing may include the sub-steps of: analog filtering the detected signals; digitizing the filtered detected signals; time domain digital filtering; frequency domain filtering including Fourier transform processing and periodogram processing; windowing to extract a desired portion of the filtered raw; various combinations of correlating and averaging spatially related signals; time-frequency processing, such as wavelet transforms. Note that windowing, for example, may be used to extract data during a linearized portion of a modulating signal (such as a Piezo drive signal). Pre-processing may also include linearization of the data to (post) compensate for non-linearities of the modulated signal. In the preferred embodiment, the periodogram of the pre-processed raw data is computed, typically by calculating the square of the fast Fourier transform (FFT) modulus of each scan or of a set of combined scans to form processed raw data. The resulting periodogram may be normalized. Scans may be split into sub-scans to improve the periodogram SNR, if needed or/and several successive scans can be combined to improve the SNR.

Referring again to FIG. 3 the step of generating a system model 305 (or parametric model) provides an ideal version of actual signals, i.e. processed signals produced by the actual OCT measurement system. The output of the system model 305 is theoretical signals 307 which are idealized actual signals. Various ways of selecting or generating the system model are discussed above. This model can include parameters related to the OCT measurement system, such as, the variation of intensity of different order reference signals determined by the reflectivity of a partial mirror and polarization effects (as described in U.S. utility Pat. No. 7,526,329 titled "Multiple Reference Non-Invasive Analysis System" and patent application Ser. No. 12/214,600, both incorporated herein).

The U.S. Pat. No. 7,526,329 patent and Ser. No. 12/214,600 patent application describe generating multiple reference signals by means of multiple reflections between a partial mirror and a mirror mounted on a piezo device. The relative magnitudes or intensities of these multiple reference signals are determined by factors where such factors include the reflectivity of the partial mirror, and may include polarization characteristics of the piezo and partial mirrors.

These multiple reference signals will generate multiple interference signals, which in the preferred embodiment are detected as a composite interference signal. When processed by periodogram or Fourier domain techniques the interference signals are manifest as peaks centered multiples of the frequency related to the first order interference signal generated by the basic scanning of the modulating Piezo device.

The system model may include parameters related to the magnitude or intensity of peaks related to interference signals. The system model also includes one or more parameters related to the interaction of the light or radiation with the target of interest. In the preferred embodiment the system model includes a parameter related to the glucose concentration in tissue fluids including, but not limited to, interstitial fluid or blood.

The theoretical signals 307 generated by the system model may be either time domain or frequency domain signals. In the preferred embodiment, the theoretical signals can be described as a collection of kernel functions, such as Gaussian kernel functions, centered on a multiple of the frequency related to the first (or a higher) order interference signal generated by the basic scanning of the modulating Piezo device.

The kernel functions may be combined in a manner that incorporates the variation of intensity (or amplitude) of different order reference signals determined by the reflectivity of the partial mirror and polarization effects and also includes at least one parameter related to the glucose concentration within tissue. The bandwidth of one or more kernel may also be used as a parameter of the model. The resulting system or parametric model is a formula representing an ideal version of theoretical signals corresponding to the actual signals that are derived by pre-processing or processing the analog signals detected by the OCT measurement system.

The inventive method includes generating a noise model 309 based on some understanding of noise sources within the actual system or derived from noise analysis of the system or a combination of both. The noise model outputs noise statistics 311. These noise statistics 311 can be generated by analyzing actual noise or may be derived from a theoretical model of various noise sources (e.g. optical source noise, mechanical noise, target noise, motion noise, detector noise, electronic noise, etc.) or some combination of the actual noise and theoretical models.

In the inventive method, a parametric estimation processor performs the step of processing outputs 313 of the actual system, the system model, and the noise model. The parametric estimation processor receives actual signals, the theoretical signals and the noise statistics and processes these inputs to generate a formula with a number of parameters, at least one of which is related to the value of an attribute of a target of interest. Processing according to the inventive method includes using estimation techniques to fit the formula to signals detected by the non-invasive analysis system to determine the value of the attribute in the target. In the preferred embodiment a formula representing the theoretical signals is fitted to the actual signals (which may be periodograms) using a maximum likelihood estimation method, and involving noise statistics, to determine the optimal values of the parameters in the theoretical signals, including the value of the parameter that is related to glucose concentration.

Typically a constrained optimization process is used to fit the system model plus noise to the resulting periodograms. Typical constraints include, but are not limited to: kernel amplitudes must be positive; there should be not more then a pre-defined number (which may be 1) of amplitude values per kernel; bandwidths must be positive and not more then some predefined limit or limits.

Referring again to FIG. 3 the method provides for outputting 315 the results of the processing step and the output is the value of at least one attribute of interest. The results of the processing step include model parameters. At least one of the model parameters includes information about at least one attribute of the target of interest and is sent to an output module. The model parameter, which in the preferred embodiment is a glucose concentration related parameter, may be output in a variety of ways, i.e. stored, displayed or made available for other operations which include, but are not limited to: controlling a device such as an insulin pump; or causing a cell phone to send a text message or pre recorded message; or controlling operation of a consumer device, such as an iPOD.

This approach described in the preferred embodiment has advantageous statistical properties and deals with an actual function, not a transformation. This approach avoids the severe impact on the noise variance for low SNR that the more typical use of a logarithmic (log) transformation and a least mean square fit of a straight line, which typically results in a poor estimation of the process, and hence the parameter to be measured (the parameter related to the glucose concentration in the preferred embodiment), particularly in a low SNR environment. If, for example, noise is additive taking the log does not preserve the noise level for every sample, since calculating the log of a sum of quantities is not equivalent to calculating the sum of the log of the quantities.

Figure 4:
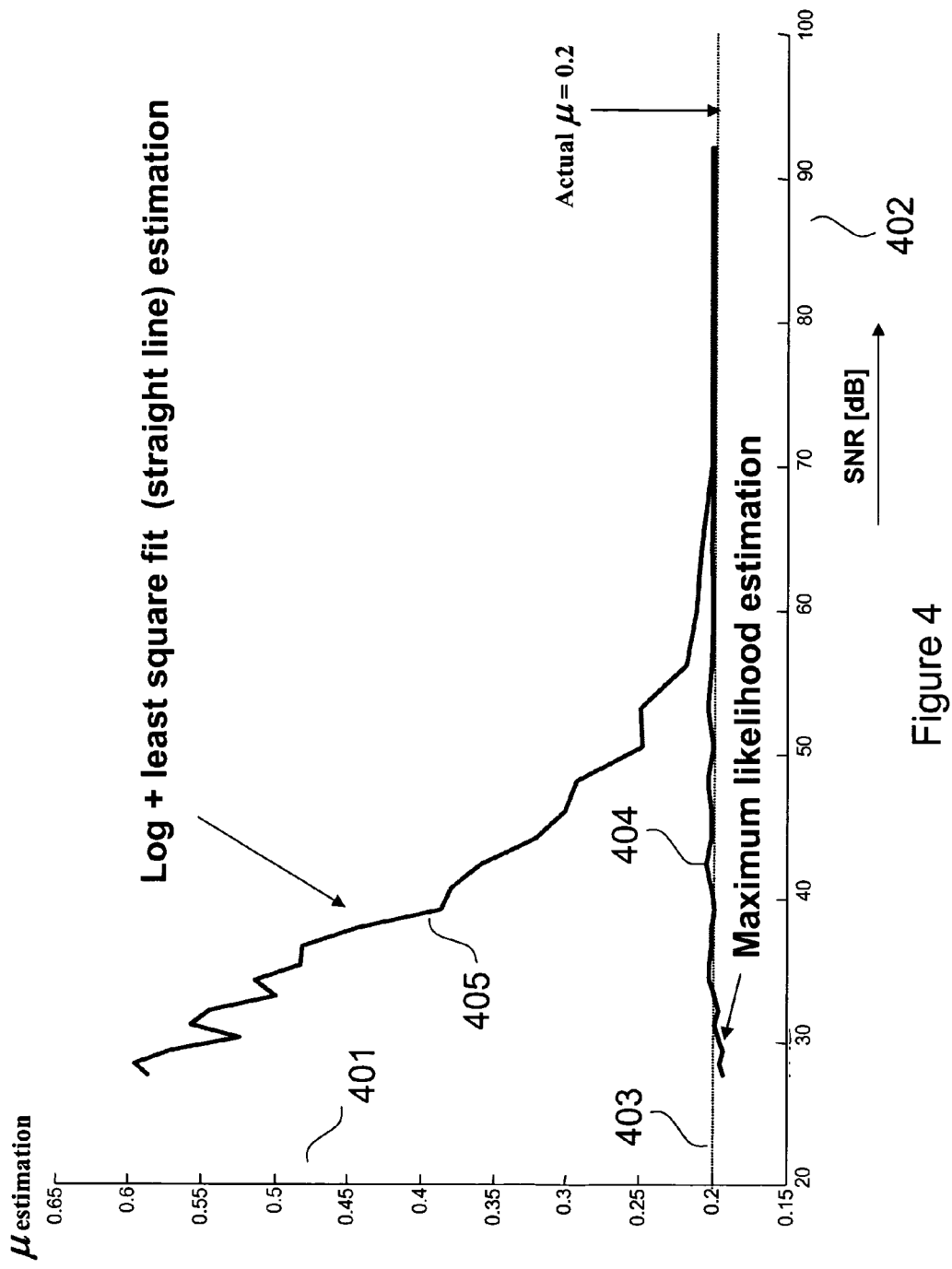
FIG. 4 is an illustration comparing, in different SNR environments, a maximum likelihood estimation technique and the logarithmic transformation plus the least mean square technique.

The plot in FIG. 4 shows the average estimations of $\mu$ (the parameter related to the glucose concentration) for several thousands of random simulations, versus the SNR (in dB). The y-axis 401, is the estimation of $\mu$ (the parameter related to the glucose concentration), while x-axis 402, is the SNR (in dB). The straight "dotted" horizontal line 403 is the actual value of $\mu$ (=0.2). The slightly varying line 404 (slightly varying from the straight line 403) is the maximum likelihood estimation variation. The crooked line 405 that significantly deviates from the straight line 403 at the low SNR range is the Log plus least square fit (straight line) estimation.

The plot in FIG. 4 confirms that low SNR environments are challenging for the logarithmic transformation and the least mean square approach, while the maximum likelihood estimation approach remains robust even in the context of low SNR. The maximum likelihood estimation approach has significantly better performance in a low SNR environment and furthermore does not assume any notion of "slope". The maximum likelihood estimation approach is therefore a noise tolerant approach to glucose measurement.

It is understood that the above description is intended to be illustrative and not restrictive. Many variations and combinations of the above embodiments are possible. Many of the features have functional equivalents that are intended to be included in the invention as being taught and many other variations of the above embodiments are possible.

The preferred embodiment above describes the invention in relation to a non-invasive analysis system, such as described in U.S. Pat. No. 7,526,329 titled "Multiple Reference Analysis System", incorporated herein by reference, however, the invention is also applicable to conventional OCT systems which translate a single reference mirror or use other conventional technologies, such as fiber stretchers or rotating diffraction gratings to achieve depth scans of tissue.

The invention is applicable to many different types of non-invasive analysis systems based on OCT systems including, but not limited to conventional time domain scanning OCT; various multiple reference based systems; Fourier OCT using either a wavelength swept source or spectral OCT using a diffraction grating to separate wavelengths.

The embodiment described use optical radiation, however the invention is not restricted to optical radiation. The invention could use other forms of radiation, including but not limited to, acoustic radiation such as ultra-sound, and other forms of electromagnetic radiation such as micro-wave or x-ray radiation. It could also use combinations of acoustic and optical radiation.

The invention is also applicable to non-invasive analysis systems for measuring glucose concentration, including but not limited to; reflective and transmissive spectroscopic approaches; photo-acoustic approaches; non-optical approaches, such as RF spectroscopy or other approaches based on measuring electrical properties of tissue or skin surface; thermal measurement approaches.

The invention is also applicable to invasive or minimally invasive analysis systems for measuring glucose concentration, including but not limited to; in-dwelling or implanted monitors; trans-dermal monitors that induce fluids through the skin surface to make glucose concentration measurements.

The invention is also applicable to non-invasive analysis systems for measuring properties other than glucose concentration, such as the concentration of analytes other than glucose. The invention is not intended to be limited to use on human targets, but should include veterinary, agricultural and botanical applications.

Other examples of application of the invention will be apparent to persons skilled in the art. The scope of this invention should be determined with reference to the specification, the drawings, the appended claims, along with the full scope of equivalents as applied thereto.

What is claimed is:

1. A non-invasive analysis system comprising:
   an OCT analysis system, said OCT analysis system outputting measurement signals containing information obtained from a target of interest;
   a system model processor configured for generating and outputting theoretical signals consistent with an idealized OCT analysis system;
   a noise model processor configured for generating and outputting noise statistics related to measurements obtained by the OCT analysis system;
   a parametric estimation processor configured to receive said measurement signals, said theoretical signals and said noise statistics and where said parametric estimation processor is configured to use at least one fitness criterion to estimate at least one model parameter used by said system model processor to optimize the fit of said theoretical signals with said measurement signals with consideration of said noise statistics; and
   an output, where said output provides information about said target of interest based on said at least one estimated model parameter.

2. The system as in claim 1, wherein the system model processor is responsive to iterative outputs of the parametric estimation processor.

3. The system as in claim 2, wherein the iterative outputs include outputs which incorporate signals from multiple targets.

4. The system as in claim 1, wherein the system model processor uses a model empirically generated by analyzing data sets and is configured to dynamically find a pattern without being predicated on the operative physics.

5. A multiple reference OCT system, said system comprising:
   a multiple reference OCT system, outputting measurement signals containing information obtained from a target of interest;
   a system model processor configured for generating and outputting theoretical signals consistent with an idealized multiple reference OCT analysis system;
   a noise model processor configured for generating and outputting noise statistics related to measurements obtained by the OCT analysis system;
   a parametric estimation processor configured to receive said measurement signals, said theoretical signals and said noise statistics and where said parametric estimation processor is configured to use at least one fitness criterion to estimate at least one model parameter used by said system model processor to optimize the fit of said theoretical signals with said measurement signals with consideration of said noise statistics; and
   an output, where said output provides information about said target of interest based on said at least one estimated model parameter.

* * * * *